United States Patent [19]

Sosnay

[11] 4,167,063

[45] Sep. 11, 1979

[54] ORTHODONTIC THREADING TOOL

[76] Inventor: Alan J. Sosnay, 55 E. 9th St., New York, N.Y. 10003

[21] Appl. No.: 842,629

[22] Filed: Oct. 17, 1977

[51] Int. Cl.² .............................................. A61C 3/00
[52] U.S. Cl. ...................................................... 32/66
[58] Field of Search ....................... 32/66; 132/89–92

[56] References Cited

U.S. PATENT DOCUMENTS 3,309,773  3/1967  Weller .................................... 32/66

Primary Examiner—Robert Peshock
Attorney, Agent, or Firm—Flynn & Frishauf

[57] ABSTRACT

An orthodontic threading tool comprises a handle portion having at one or both ends thereof a shank portion extending from the handle portion, a loop portion extending from the shank portion and a threading portion extending from the loop portion. The loop portion extends from the shank in the direction away from the longitudinal axis of the shank. The threading portion extends away from the loop portion such that at least part of the threading portion is located on the opposite side of the longitudinal axis of the shank from that of the loop portion. The threading portion has a curved or bent area defining a camming or bearing surface along which said threading portion is engageable with an arch wire or the like so as to permit a revolving action of the free end of the threading portion about the arch wire or the like. A hook member is provided at the free end of the threading portion for engaging an orthodontic thread, or the like.

23 Claims, 7 Drawing Figures

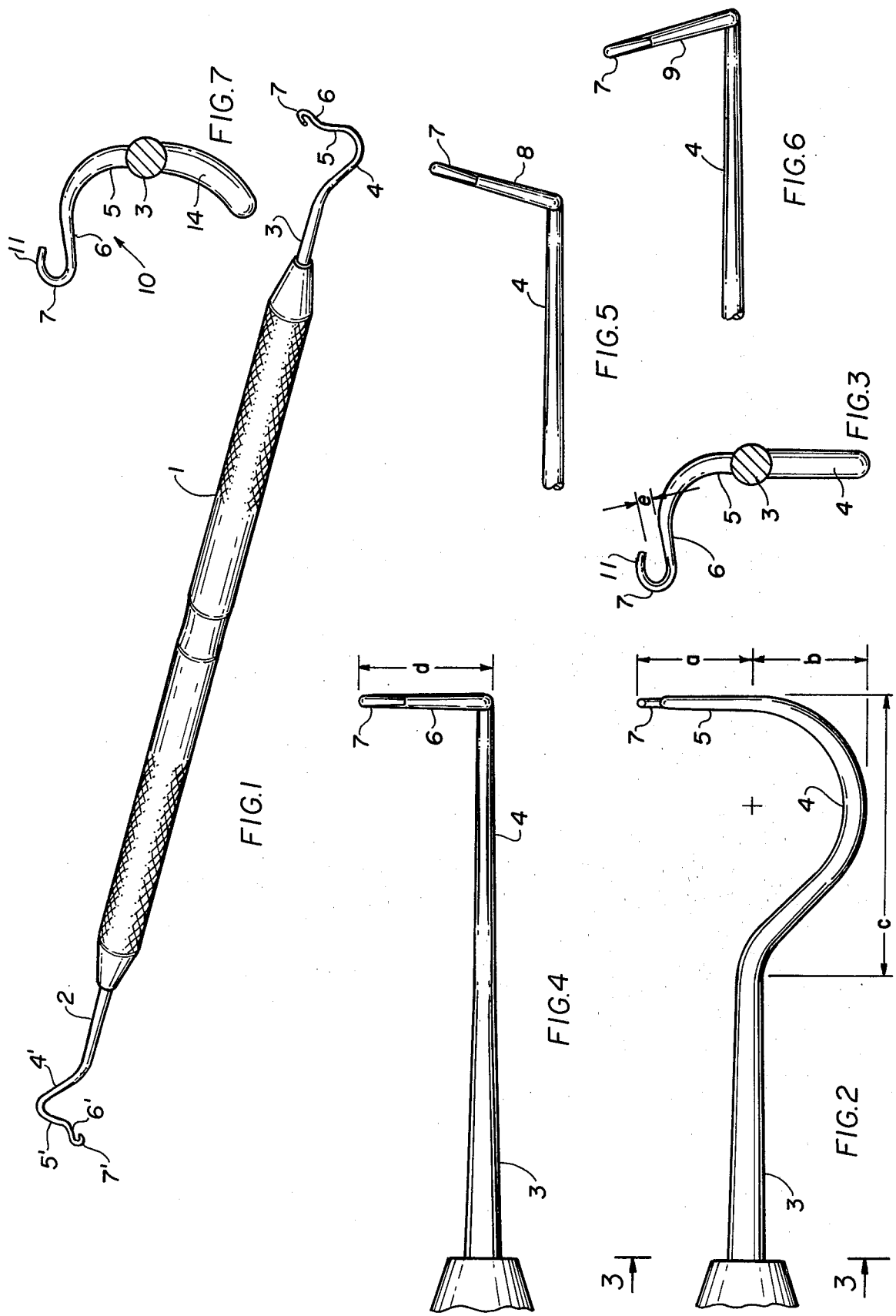

ORTHODONTIC THREADING TOOL

This invention relates to an orthodontic threading tool.

During orthodontic treatment, it is often necessary to thread orthodontic elastic threads, or other elongated orthodontic elements, between adjacent brackets on respective teeth and behind an orthodontic arch wire which is already mounted in place on the various brackets. Difficulty has been encountered in conducting such threading. This is due to the restricted dimensions of the area involved and the impediment to threading by the protruding gingival tissues.

It is the object of the present invention to provide a simple and inexpensive orthodontic threading tool which is easy to fabricate and which is easy to use under a large variety of operating conditions.

SUMMARY OF THE INVENTION

In accordance with the present invention, an orthodontic threading tool comprises a handle portion having at one or both ends thereof a shank portion extending from the handle portion, a loop portion extending from the shank portion and a threading portion extending from the loop portion. The loop portion extends from the shank in a direction away from the longitudinal axis of the handle. The threading portion extends away from the loop portion such that at least part of the threading portion is located on the opposite side of the longitudinal axis of the handle from that of the loop portion. The threading portion has a curved or bent area defining a camming or bearing surface along which said threading portion is engageable with an arch wire or the like so as to permit a revolving action of the free end of the threading portion about the arch wire or the like. A hook member is provided at the free end of the threading portion for engaging an orthodontic thread, or the like.

In a preferred embodiment, the shank, loop portion and threading portion are an integral bent wire member. The loops and threading portions at the opposite ends of the shank are oppositely directed so that a thread may easily be grasped from above and below the arch wire (in the interproximal region of the teeth) and drawn behind the arch wire in the conventional figure "8" method of threading elastic ligatures and the like. It also permits ease of use in all four dental quadrants (upper right, upper left, lower left, lower right). In a further preferred arrangement, the threading portion has a free end which extends at an angle of slightly less than 90° to the plane of the loop portion.

BRIEF DESCRIPTION OF THE DRAWINGS

FIG. 1 is a perspective view of an orthodontic threading tool according to the present invention;

FIG. 2 is an enlarged partial side view thereof;

FIG. 3 is an enlarged cross sectional view thereof taken along line 3—3 in FIG. 2;

FIG. 4 is an enlarged partial top view of the portion shown in FIG. 2;

FIG. 5 is an enlarged partial view of a modified embodiment of the invention;

FIG. 6 is an enlarged partial view of another modified embodiment of the invention; and FIG. 7 is an enlarged cross section view (similar to that of FIG. 3) of a further modified embodiment of the invention.

DETAILED DESCRIPTION

Referring to FIG. 1, the orthodontic threading tool of the present invention comprises a handle portion 1 which preferably has a knurled surface or other non-slip gripping surface. Extending from the respective ends of handle 1 are respective shanks 2 and 3 which have a substantially smaller diameter than handle 1. The ends of the respective shanks 2 and 3 are formed into threading arrangements. One of the threading arrangements will be described in detail, the other threading arrangements at the opposite end of the handle being similar, but designed for threading in a counter-rotational manner so that the ligatures may be easily grasped from above and below the arch wire in all four dental quadrants. The elements of the threading arrangement at said opposite end of the handle are denoted by primed reference numerals.

Referring to FIGS. 1-4, a loop portion 4 extends from the metallic wire shank 3. The loop portion 4 extends away from the longitudinal axes of the shank 3 and handle portion 1, and preferably laterally from said longitudinal axis. Preferably, the longitudinal axes of shanks 2 and 3 are coaxial with the longitudinal axis of handle portion 1. A threading portion 10, comprising leg members 5 and 6, extends from loop 4 so that at least part of the threading portion 10 (i.e., at least leg 6) is located on the opposite side of the longitudinal axis of shank 3 from that of the loop portion 4. Leg 6 preferably extends a predetermined distance past the axis of the shank 3. The threading portion 10 changes direction on said other side of said longitudinal axis of shank 3 so as to become generally "L" shaped, as best seen in FIG. 3. Thus, there is an angle of approximately 90° between legs 5 and 6 of the threading portion 10. The curve or bend between legs 5 and 6 need not be sharp as shown in FIG. 3—the curve or bend may be made more gently curved, as desired, and the angle between legs 5 and 6 may be varied. In a preferred embodiment, the leg 6 extends from leg 5 at an angle of approximately 90° relative to the longitudinal axis of shank 3, as best seen in FIG. 4. Other angular relationships may be used, as will be discussed hereinafter with reference to FIGS. 5 and 6. The leg 6 of threading portion 10 has a hook 7 formed at the free end thereof for engaging elongated orthodontic threads, either of the elastic variety or of the non-elastic variety, or other orthodontic elements such as spring wires, uprighting springs, or the like.

Hook 7 includes a curved hook portion 11 which is curved back toward the second leg 6 and which extends in a direction away from the longitudinal axis of the handle 1. The free end of the curved hook portion 11 is directed toward the second leg 6 to form a generally "C" shaped configuration with the confronting portion of the second leg 6. This substantially prevents the free end of the curved hook portion 11 from injuring gingival tissue during operation of the tool. The second leg 6 has a curved area in the vicinity of the hook 7, and preferably just in front of the hook 7, to further protect gingival tissue from the free end of the hook portion on disengagement of the tool from an arch wire or the like.

Leg portions 5 and 6 of threading portion 10 are preferably integrally formed from metal wire or plastic, preferably metal, with a curve or bend therebetween. The area of the bend in the vicinity of the junction between legs 5 and 6 serves as a bearing or camming surface along which the threading portion 10 is engageable with an arch wire or the like so as to permit a revolving action of the free end (i.e., hook 7 end) of the threading portion 10 about the arch wire or the like, thereby facilitating operation in the patient's mouth.

In a preferred embodiment, the dimensions a, b, c, d and e, as illustrated in FIGS. 2 and 3, are as follows:
 a=0.170 inches
 b=0.160 inches
 c=0.400 inches
 d=0.185 inches
 e=0.034 inches Preferably, the shank 3, loop 4, leg portions 5 and 6 and hook 7 are formed from a single piece of tapered bent metallic wire. In a preferred embodiment, the diameter of the wire varies from about 0.05 inches at the thickest part of the shank 3 to from about 0.015 to about 0.025 inches at the end of the hook 7. The dimensions of course may vary, as desired.

The bend or curve between the legs 5 and 6 of threading portion 10, which is preferably at an angle of slightly less than 90°, provides a bearing or camming surface in the vicinity of the bend or curve so as to serve as a convenient bearing or camming surface along which the arch wire may be slidingly engaged. This permits a revolving action of the threading portion 10 while bearing against the arch wire already installed in the mouth so as to facilitate the insertion and retraction of the free end of the threading portion behind the arch wire. Moreover, since the bend between leg portions 5 and 6 is relatively close to the axis of shank 3, the axis of shank 3 may be aligned close to the longitudinal axis of the arch wire to facilitate orientation of the tool in the patient's mouth. Further, a more convenient operation may be obtained merely by turning or revolving the handle 1 between the fingers without requiring a substantial lateral displacement of the handle 1 during turning thereof. The threading may be accomplished by a simple substantially rotational movement, rather than requiring a substantial transverse or lateral movement in addition to the rotational movement.

Still further, since the leg 6 of threading portion 10 extends at a relatively sharp angle from the leg 5, as contrasted with the prior art devices, the threader may be passed behind an arch wire, the camming surface being brought to bear on the arch wire, and the tool turned between the fingers while camming on the arch wire to locate the hook in a thread-receiving position without danger of hurting the patient. Due to the sharp angle between legs 5 and 6, the hook remains relatively far from the patient's gingival tissue during insertion of the tool and during threading.

While the angle between legs 6 and 5 is preferably less than 90°, the angle could be equal to 90° or slightly greater, as desired. However, when the angle is somewhat less than 90°, convenient operation is assured. The bend between legs 5 and 6 may be relatively sharp, as shown, or may be a gentle curve. Each curve results in a desired orientation of legs 5 and 6. Also, it should be clear that the thickness of the shanks 2 and 3, at the ends thereof which form the threading portion of the tool, can vary, depending upon application and the type of wire or other materials used therefor. Additionally, the dimensions a, b, c, d and e can vary while still providing satisfactory results.

By having the loop portion 4 extending laterally to one side of the axis of the shank 3 while the threading portion 10 extends to the opposite side of the shank 3, causes the longitudinal axis of the handle and the longitudinal axis of the shank to be located between the loop portion 4 and the threading portion 10. This results in the following advantages:

1. The handle may be placed parallel with the arch wire which is the most preferred orientation while working;
2. A simple and minimal rotating action of the handle on its longitudinal axis will initiate the threading action of hook 7 in the interproximal region behind and around the arch wire with its camming or bearing surface engaging the arch wire. This action serves to keep the threading device free of the impinging gingival tissues. In addition, distributing the threading portion opposite from the loop portion serves to allow for greater movement of the hook portion outward from the teeth and the arch wire, thereby facilitating easy engagement of the thread with the hook.

The area within loop portion 4 (interloop region) enables greater rotation of the threading instrument by reducing or avoiding cuspal impingement of the teeth. The greater rotation permits the hook 7 to be oriented further away from the arch wire, to facilitate grasping of the thread by the hook 7. This is a particular advantage when the loop is oriented on the occlusal side of the arch wire during the threading process.

FIGS. 5 and 6 illustrate top view of modified embodiments of the invention similar to that of FIG. 4. In FIGS. 5 and 6, similar reference numerals are used where applicable. In FIG. 5, the leg 8, which corresponds to the leg 6 in FIGS. 1-4, is at an angle somewhat greater than 90° with respect to the longitudinal axis of shank 3. In some applications, for example, when working in the front portions of a mouth, this angular orientation can be desirable. In FIG. 6, the leg 9, which corresponds to the leg 6 in FIGS. 1-4, is at an angle of less than 90° with respect to the longitudinal axis of the shank 3. This angulation of leg 9 may be particularly advantageous when working in the rear portion of a mouth so that the hook which extends from the leg 9 will be closer to the front of the mouth so that the orthodontist may more easily observe the threading operation and may more easily engage the orthodontic thread with the hook 7. The tools shown in FIGS. 5 and 6 are preferably double-ended tools, for example as shown in FIG. 1.

FIG. 7 illustrates a modification where the loop portion 14 is further curved in a direction toward the leg 6 of threading portion 10. This arrangement permits even greater rotation of the instrument around its longitudinal axis to furthe facilitate threading.

Preferably, the threading arrangements at the end of the shanks 2, 3 in all of the embodiments of the present invention are formed from bent wire so that all of the portions of the threading arrangement are integral. The wire from which the threading arrangement is fabricated may be a constant diameter thin wire, or may be tapered, with the thinner portions at the hook end thereof.

While the invention has been described above with respect to specific embodiments, it should be clear that various modifications and alterations may be made within the scope of the present inventive concept, as set forth in the appended claims.

I claim:
1. An orthodontic threading tool, comprising:
 a handle portion (1) having a longitudinal axis;
 at least one shank portion (3) extending from an end of said handle portion (1);

a loop portion (4) extending from said shank portion (3) in a direction away from said longitudinal axis of said handle portion;

a threading portion (10) extending from said loop portion (4) in a direction such that at least part of said threading portion (10) is located in close proximity to said longitudinal axis of said handle portion;

said threading portion (10) including a first leg (5) extending from said loop portion and a second leg (6) extending from said first leg, said first and second legs forming a generally "L" shaped arrangement, said threading portion (10) further including a curved or bent area at least at the juncture of said first and second legs defining a camming or bearing surface along which said threading portion (10) is contact-engageable with an arch wire or the like, said camming or bearing surface being in close proximity to a line extending along said longitudinal axis of said handle portion so that a revolving action of said handle portion substantially about said longitudinal axis thereof imparts a revolving action to said camming or bearing surface about the arch wire or the like; and a hook member (7) at a free end of said second leg (6) of said threading portion (10) for engaging orthodontic threads or other elongated elements of both the elastic and non-elastic variety and other orthodontic elements such as spring wires, uprighting spring, or the like;

the length of said second leg (6) being such that when said handle portion is revolved about its longitudinal axis and said camming or bearing surface is in engagement with the arch wire or the like, said second leg (6) extends outwardly of said arch wire or the like to permit engagement of said hook member (7) with said orthodontic threads or said other orthodontic elements.

2. Orthodontic threading tool according to claim 1 wherein said first and second legs are at an angle of approximately 90° relative to each other.

3. Orthodontic threading tool according to claim 1 wherein said loop portion extends in a plane which includes said longitudinal axis of said handle portion.

4. Orthodontic threading tool according to claim 1 wherein said shank portion has a longitudinal axis which is substantially coaxial with said longitudinal axis of said handle portion.

5. Orthodontic threading tool according to claim 4 wherein said threading portion extends from said loop portion generally transversely to said longitudinal axis of said handle portion and crosses said longitudinal axis of said handle portion.

6. Orthodontic threading tool according to claim 5 wherein said second leg (6) of said threading portion extends substantially transversely to the longitudinal axis of said handle, and extends at an angle of appoximately 90° relative to said first leg (5) of said threading portion.

7. Orthodontic threading tool according to claim 1 wherein said shank portion, loop portion, threading portion and hook member are fabricated from a single piece of metallic wire.

8. Orthodontic threading tool according to claim 7 wherein said wire is tapered toward said hook member.

9. Orthodontic threading tool according to claim 1 wherein said hook member is directed away from the longitudinal axis of said handle portion.

10. Orthodontic threading tool according to claim 1 wherein said threading portion has a first leg (5) extending from said loop portion and a second leg (6) extending from said first leg on the side of said longitudinal axis of said handle portion opposite to the side thereof on which said loop portion extends, and said second leg being oriented at an angle of greater than 90° relative to said longitudinal axis of said handle portion.

11. Orthodontic threading tool according to claim 1 wherein said threading portion has a first leg (5) extending from said loop portion and a second leg (6) extending from said first leg on the side of said longitudinal axis of said handle portion opposite to the side thereof on which said loop portion extends, and said second leg being oriented at an angle of less than 90° relative to said longitudinal axis of said handle portion.

12. Orthodontic threading tool according to claim 1 wherein said loop lies in a curved plane.

13. Orthodontic threading tool according to claim 1 wherein said first and second legs are at an angle of less than 90° relative to each other.

14. Orthodontic threading tool according to claim 13 wherein said first and second legs are at an angle of slightly less than 90° relative to each other.

15. Orthodontic threading tool according to claim 1 wherein said second leg is oriented at an angle of greater than 90° relative to said longitudinal axis of said handle portion.

16. Orthodontic threading tool according to claim 1 wherein said second leg is oriented at an angle of less than 90° relative to said longitudinal axis of said handle portion.

17. Orthodontic threading tool according to claim 1 wherein said revolving action of said camming or bearing surface about the arch wire or the like is carried out with the camming or bearing surface in contact-engagement with the arch wire or the like.

18. Orthodontic threading tool according to claim 1 wherein at least part of said threading portion (10) is located on the opposite side of said longitudinal axis of said handle portion from that of said loop portion.

19. Orthodontic threading tool according to claim 9 wherein said hook member (7) includes a curved hook portion (11) curved back toward said second leg (6) and extending in a direction away from said longitudinal axis, the free end of said curved hook portion (11) being directed toward said second leg (6) to form a generally "C" shaped configuration with the confronting portion of said second leg (6) to substantially prevent said free end of said curved hook portion (11) from injuring gingival tissue during operation of the tool.

20. Orthodontic threading tool according to claim 19 wherein said hook member (7) is integral with said second leg (6).

21. Orthodontic threading tool according to claim 19 wherein said second leg has a curved area in the vicinity of said free end of said curved hook portion (11) to further protect gingival tissue from impingement by said free end of said curved hook portion on disengagement of said tool from said arch wire or the like.

22. Orthodontic threading tool according to claim 9 wherein said hook member (7) includes a hook portion (11) curved back towards said second leg (6), said hook portion (11) having a free end, said second leg (6) having a curved area in the vicinity of said free end of said hook portion (11) to protect gingival tissue from impingement by said free end of said hook portion on disengagement of said tool from said arch wire or the like.

23. Orthodontic threading tool according to claim 9 wherein said hook member (7) is integral with said second leg (6).

* * * * *